(12) United States Patent
Hossack et al.

(10) Patent No.: US 6,612,992 B1
(45) Date of Patent: Sep. 2, 2003

(54) MEDICAL DIAGNOSTIC ULTRASOUND CATHETER AND METHOD FOR POSITION DETERMINATION

(75) Inventors: John A. Hossack, Charlottesville, VA (US); Michael G. Curley, Cambridge, MA (US); Thilaka S. Sumanaweera, San Jose, CA (US); John I. Jackson, Menlo Park, CA (US)

(73) Assignee: Acuson Corp, Mountain View, CA (US)

( * ) Notice: Subject to any disclaimer, the term of this patent is extended or adjusted under 35 U.S.C. 154(b) by 0 days.

(21) Appl. No.: 09/516,868

(22) Filed: Mar. 2, 2000

(51) Int. Cl.[7] ................................................ A61B 2/00
(52) U.S. Cl. ..................................................... 600/467
(58) Field of Search ................................. 600/443, 459, 600/461, 460, 462, 463, 447, 437, 442

(56) References Cited

U.S. PATENT DOCUMENTS

| 5,415,175 | A |   | 5/1995  | Hanafy et al. |         |
|-----------|---|---|---------|---------------|---------|
| 5,538,004 | A |   | 7/1996  | Bamber        |         |
| 5,563,810 | A |   | 10/1996 | Cherry et al. |         |
| 5,633,494 | A |   | 5/1997  | Danisch       |         |
| 5,728,044 | A |   | 3/1998  | Shan          |         |
| 5,797,849 | A |   | 8/1998  | Vesely et al. |         |
| 5,876,345 | A |   | 3/1999  | Eaton et al.  |         |
| 5,899,860 | A | * | 5/1999  | Pfeiffer et al. | 600/424 |
| 5,928,151 | A |   | 7/1999  | Hossack et al. |        |
| 5,984,869 | A |   | 11/1999 | Chiao et al.  |         |
| 6,014,473 | A |   | 1/2000  | Hossack et al. |        |
| 6,165,127 | A | * | 12/2000 | Crowley       | 600/439 |
| 6,233,476 | B1 | * | 5/2001 | Strommer et al. | 600/424 |
| 6,266,552 | B1 | * | 7/2001 | Slettenmark   | 600/424 |
| 6,275,724 | B1 | * | 8/2001 | Dickinson et al. | 600/424 |

OTHER PUBLICATIONS

Transom Technologies, Inc., Transom Corporate Overview; pp. 1–5.

* cited by examiner

*Primary Examiner*—Marvin M. Lateef
*Assistant Examiner*—Maulin Patel

(57) ABSTRACT

A catheter and method for determining a position of the catheter within the cardiovascular system is provided. Local bending and twisting is measured at multiple locations along the catheter. By integrating the measurements, the position and orientation of the catheter is determined. Based on the catheter position information, the location and orientation of an ultrasound transducer array connected with the catheter is known. The imaging array position and orientation information may be used to assist a physician in determining the tissue structure or fluid being scanned and/or assist in the accurate generation of three-dimensional representations.

25 Claims, 3 Drawing Sheets

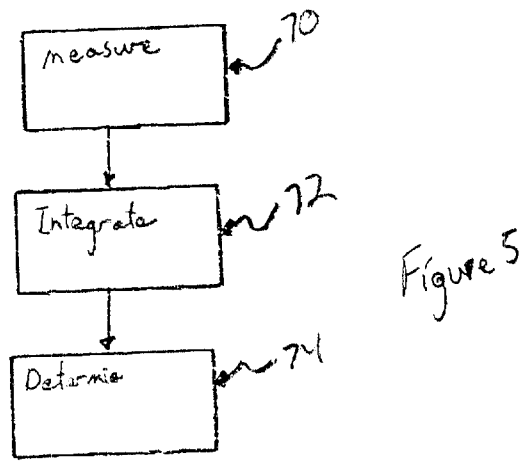
Figure 5
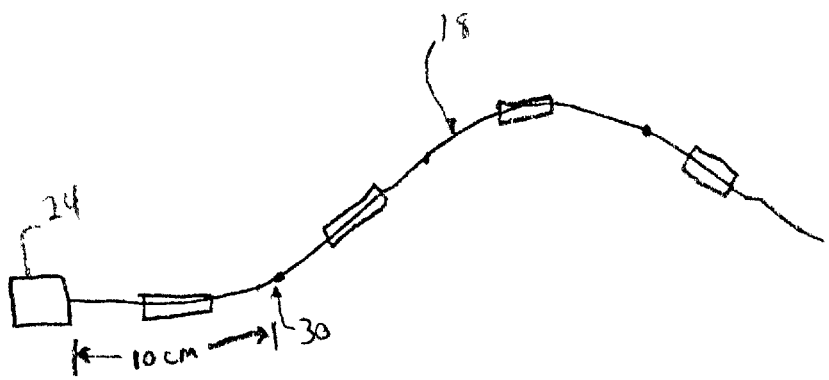
Figure 6
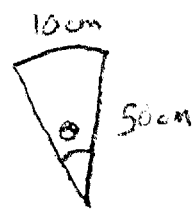
$$\theta \sim \frac{10}{2\pi \cdot 50} \cdot 360° = 11.5°$$
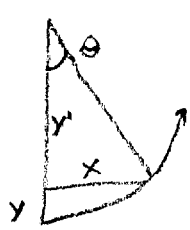
$$x = 50 \sin(\theta) = 9.97$$
$$y \to 50 - y\left(\frac{x}{50} - \cos(\theta)\right) \quad y = 1.00$$

US 6,612,992 B1

MEDICAL DIAGNOSTIC ULTRASOUND CATHETER AND METHOD FOR POSITION DETERMINATION

BACKGROUND

This invention relates to a medical diagnostic ultrasound catheter and method for position determination. In particular, deformation of a catheter is measured locally to determine the position of a transducer array on the catheter.

Catheters are used for ultrasonic examination of the heart or the vascular system. A transducer array of piezoelectric elements is positioned on the catheter. The catheter is inserted through the circulatory system so that the transducer array is positioned near or within the heart of a patient. However, bending and twisting of the catheter results in ambiguity of the position of the imaging scan plane. Without information on the orientation of the transducer array, a physician relies on image recognition. The images may be from different viewpoints and appear upside down or out of position with respect to the physician's intuitive understanding of the anatomy.

U.S. Pat. No. 5,876,345 to John W. Eaton et al. discloses two different structures and associated methods for identifying a position of an imaging array on a catheter. In one method, data obtained from an ultrasound scan is used to determine the direction and amount of motion that the arrays have traveled. In the second method, an absolute position sensor, such as a magnetic position sensor, is used to determine the location of the imaging array.

Other types of sensors have been used on colonoscopes. In U.S. Pat. No. 5,728,044, Shan discloses placing strain gauges on a sensor device. Strain gauges are used for torsional and bending measurements. The sensor device is inserted within a colonoscope. However, for imaging calculations, Shan suggests using a sensor device without torsional strain gauges at Col. 6, lines 16–21.

BRIEF SUMMARY

The present invention is defined by the following claims, and nothing in this section should be taken as a limitation on those claims. By way of introduction, the preferred embodiment described below includes a method and catheter for determining a position of the catheter within the cardiovascular system. Local bending and twisting is measured at multiple locations along the catheter. By integrating the measurements, the position and orientation of the catheter is determined. Based on the catheter position information, the location and orientation of an ultrasound transducer array connected with the catheter is known. The imaging array position and orientation information may be used to assist a physician in determining the tissue structure or fluid being scanned and/or assist in the accurate generation of three-dimensional representations.

In one aspect, a medical diagnostic ultrasound imaging catheter for determining a catheter position within a cardiovascular system is provided. A flexible catheter rod comprises a shaft portion and a distal end portion. An ultrasound transducer operatively connects with the distal end portion. A plurality of local deformation sensors are spaced along the catheter rod.

In a second aspect, a method for determining a position of a medical diagnostic ultrasound imaging catheter within a cardiovascular system is provided. A local deformation is measured at each of a plurality of locations along the catheter. The local deformation measurements are integrated, and a position on the ultrasound transducer array is determined as a function of the integrated local deformation measurements.

Further aspects and advantages are discussed below in conjunction with the preferred embodiments.

BRIEF DESCRIPTION OF SEVERAL VIEWS OF THE DRAWINGS

FIG. 5 is a flow chart diagram representing a method for determining the position of a catheter.

FIG. 6 is a graphical representation of a deformed catheter.

DETAILED DESCRIPTION OF THE PREFERRED EMBODIMENTS

The position and orientation of an ultrasound transducer imaging array in a tip or other position in an ultrasound catheter is obtained with local deformation sensors. Deformation sensors measure the bending or twisting at multiple local regions along the catheter. The multiple local measurements are integrated to derive the position and orientation information. The position and orientation is determined with respect to the insertion point or handle of the catheter.

Figure 1:
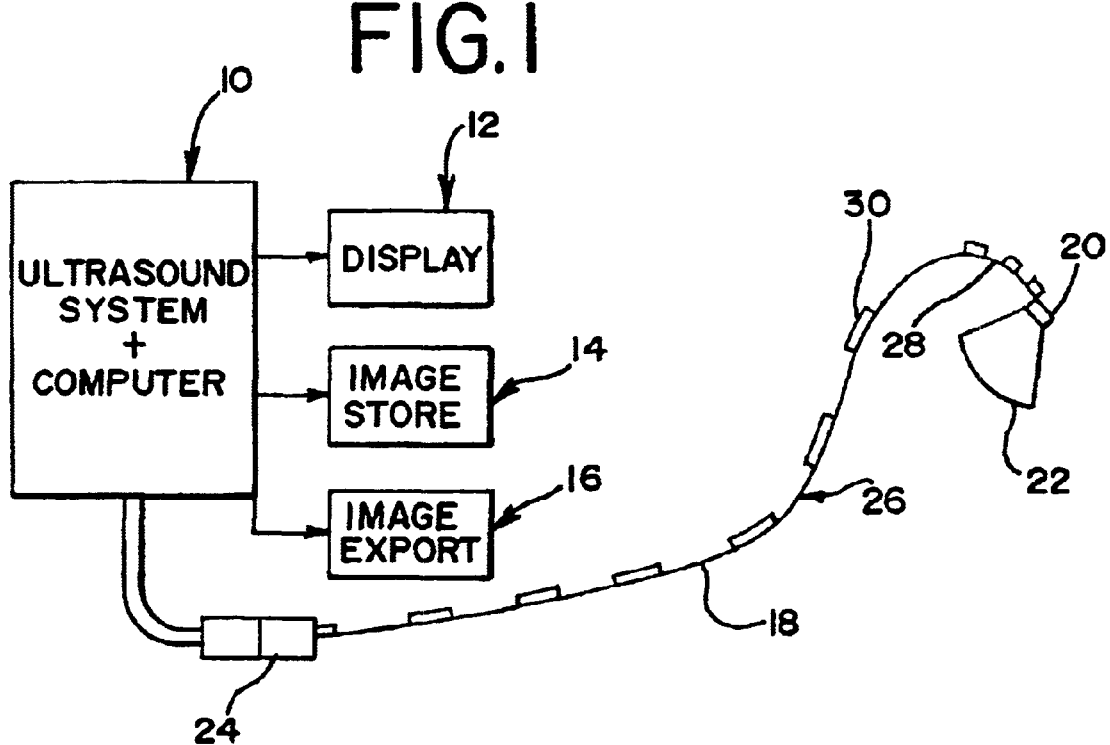
FIG. 1 is a block diagram of a medical diagnostic ultrasound system and associated catheter for obtaining ultrasound image information and determining the position of an ultrasound transducer array on the catheter.

FIG. 1 shows a block diagram of one preferred embodiment of an ultrasound system and catheter for determining the position of a transducer array within a patient. This embodiment includes an ultrasound system 10, a display 12, an image storage device 14, an image export device 16 and a catheter 18.

The ultrasound system 10, the display 12, the image storage device 14, and the image export device comprise a medical diagnostic ultrasound system. For example, the Sequoia®, Aspen™, or the 128 XP® ultrasound systems manufactured by Acuson Corporation are used, but other ultrasound systems from other manufacturers may be used. In alternative embodiments, the image storage device 14 and/or the image export device 16 are not provided. The ultrasound system 10 receives echo information from the catheter 18. The echo information is processed.

The ultrasound system 10 operates in one or more various modes, such as B-mode, flow mode (e.g. color Doppler mode), and/or spectral Doppler mode. The echo information is processed to isolate information at fundamental frequencies, harmonic frequencies, or combinations thereof. The data is then scan converted to generate an image on the display 12. The image is optionally stored on the image storage device 14, such as a CINE or video loop memory storage, and is optionally exported by the image export device 16, such as a modem or other interface for exporting DICOM or other images.

The catheter 18 comprises an ultrasound transducer array for scanning a region of a patient as represented by a scan plane 22, a handle 24, a shaft portion 26, a distal end portion 28 and a plurality of deformation sensors 30. For example, the catheter 18 comprises a catheter sold as the AcuNAV™ transducer sold by Acuson Corporation. The ultrasound transducer array 20 comprises an array of piezoelectric elements electrically connected with the ultrasound system 10. The ultrasound array 20 is a one dimensional, 1.5 dimensional, two dimensional, or other array. For example, an array disclosed in U.S. Pat. No. 5,876,345, the disclosure of which is incorporated herein by reference, is used. In an alternative to piezoelectric elements, electrostatic elements are provided. Another example is a transducer array taught in U.S. Pat. No. 5,415,175, the disclosure of which is incorporated herein by reference.

The shaft portion 26 and the distal end portion 28 comprise a catheter rod. The distal end portion 28 and shaft portion 26 comprise one continuous element or may be two separate components connected together. The catheter shaft portion 26 and distal end portions 28 preferably comprise flexible material, such as one or more guide wires or other components for stiffness and torsion control surrounded by a molded polyurethane or Pebax™, available from Atochem. In one embodiment, the distal end portion 28 is more flexible (e.g., made from Tecothane™ from Thermomedics Inc.) than the shaft portion 26 (e.g., made from Pebax™).

The deformation sensors 30 comprise devices for measuring an amount of twisting or bending at a location along the shaft portion 26 or distal end portion 28 of the catheter 18. In one preferred embodiment, the deformation sensors 30 comprise strain gauges, such as available from Measurements Group, Inc. of Raleigh, N.C. The deformation sensors 30 are spaced to determine an amount of bending and/or twisting at a plurality of locations along the catheter 18. For locations between the deformation sensors 30, the local bending or twisting is estimated by interpolation from the measurements at adjacent sampled regions of the catheter 18. In addition to linear interpolation, other curve fitting, such as cubic splines, may be used for improved accuracy.

In one embodiment, one deformation sensor 30 is used for measuring the amount of twisting of the catheter 18. Assuming the bulk of the resistance to twist is generated near the distal end portion 28, a measurement of the twist near the handle 24 (i.e., proximal end) and the catheter entry point is used to estimate the net catheter twist. For more accurate determinations of twist, additional twisting deformation sensors 30 may be used. Experimentation may provide the optimal number of twisting deformation sensors 30 using such considerations as expense, complexity and performance.

The plurality of deformation sensors 30 are spaced along the catheter 18. In one embodiment, a single deformation sensor 30 detects bending. Preferably, a plurality of deformation sensors 30 detect bending and are spaced apart as a function of the flexibility of the catheter. The more rigid portions of a catheter 18 have fewer deformation sensors than the more flexible portions. In one embodiment, deformation sensors for measuring bending are spaced at 10 centimeter intervals along the more rigid shaft portion 26 and at 6 centimeter intervals along the more flexible distal end portion 28. Other spacings may be used including more dense or less dense spacing.

Figure 2:
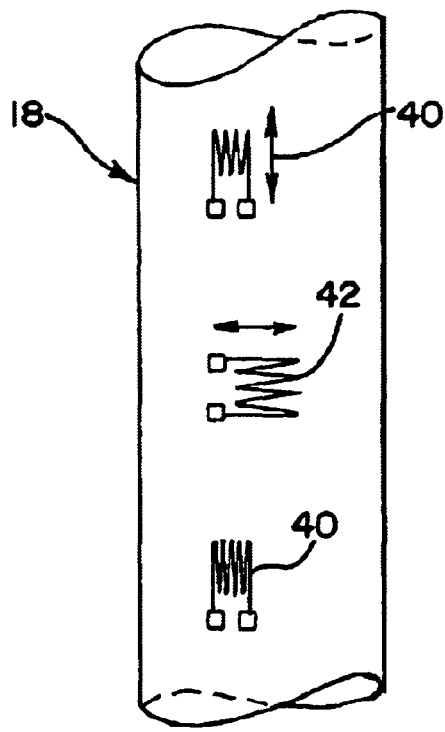
FIG. 2 is a partial cutaway view of an ultrasound catheter with deformation sensors.

Referring to FIG. 2, the portion of a catheter is shown with strain gauges as the deformation sensors 30. Two bending strain gauge deformation sensors 40 and a single twisting strain gauge deformation sensor 42 are shown. The bending strain gauge deformation sensors 40 measure the amount of bending within a plane intersecting and parallel with a neutral axis of the catheter and intersecting the bending strain gauge deformation sensor 40. The twisting strain gauge deformation sensor 42 measures the amount of relative rotation between two adjacent points spaced away from the neutral axis of a catheter. For example, the twisting strain gauge deformation sensors are positioned to measure strain at a 90° C. angle to the neutral axis. In alternative embodiments, the strain gauge deformation sensors 40, 42 are positioned to be at different angles to the neutral axis of the catheter (e.g., at an angle other than parallel or 90° C. to the axis).

Figure 3:
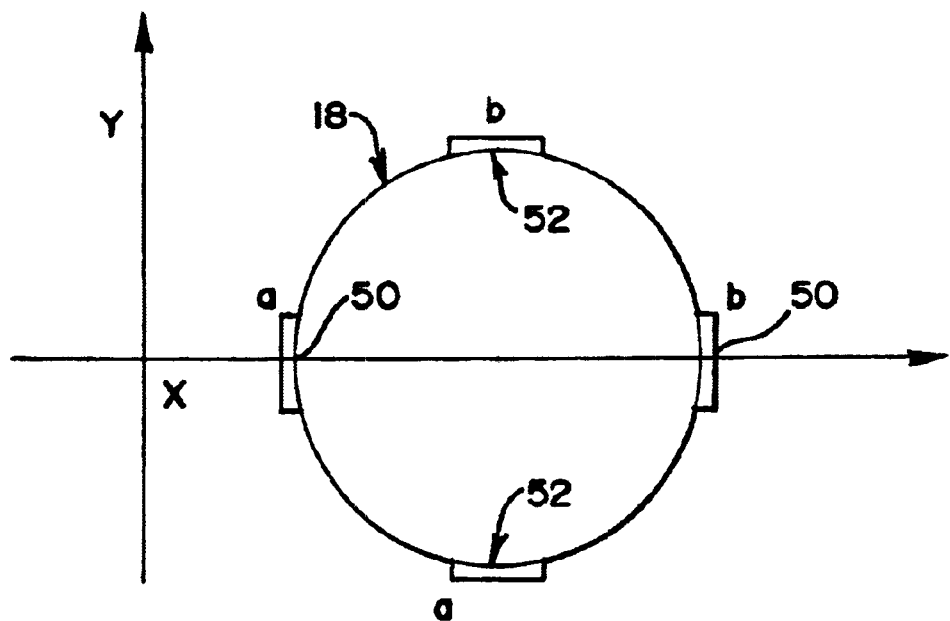
FIG. 3 is a cross-sectional view of the catheter of FIG. 2.

In one preferred embodiment, a plurality of deformation sensors 30 are provided for each measurement location along the catheter 18. For example, FIG. 3 shows a cross section through the catheter 18 of FIG. 2. The axis of the catheter 18 is along a z axis. One pair 50 of strain gauges is placed on the catheter 18 along the x axis and a second pair 52 of strain gauges are placed on the catheter 18 along the y axis. As shown, the strain gauges 50, 52 are positioned at 90° C. intervals around the circumference of the catheter 18. In alternative embodiments, one strain gauge in the x axis and one strain gauge in the y axis, additional pairs of strain gauges, or combinations of single and paired strain gauges are used. By providing a strain gauge in two different planes, bending along two major axi is determined.

Figure 4:
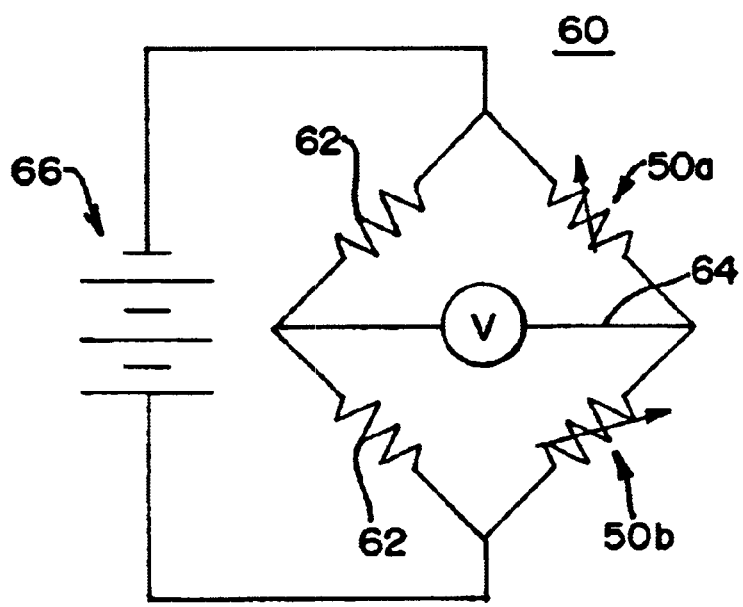
FIG. 4 is a circuit diagram of one preferred embodiment of strain gauge deformation sensors.

FIG. 4 shows one preferred embodiment for providing paired strain gauges as discussed above. A Wheatstone bridge circuit 60 is used to measure the strain at two positions in the same plane around the circumference of the catheter 18. For example, two strain gauges represented by variable resistance 50a and 50b comprise the paired strain gauges 50 of FIG. 3. A pair of resistors 62 is also provided, and is selected to match the resistances of the strain gauges 50a and 50b when the catheter 18 is at rest position. A voltage source 66 provides potential to the Wheatstone bridge circuit 60. Preferably, the voltage source 66 comprises a DC voltage. A voltmeter 64 measures the potential in the Wheatstone bridge as a measurement or estimation of the amount of strain. The twisting strain gauge deformation sensor 42 of FIG. 2 likewise comprises a Wheatstone bridge circuit with one or preferably two or more variable resistances. For either twisting or bending deformation sensors 40, 42, different types of strain gauges, and/or associated circuits may be used, such as semiconductor strain gauges and/or direct measurement of potential across the strain gauge connected in series with a known fixed resistor.

FIG. 5 shows one embodiment for determining the location of an ultrasound transducer array using local measurements of bending and/or twisting. Local bending or twisting is measured in act 70. In act 72, the measurements are integrated to determine the position of the catheter 18. The position of the transducer array is determined from the integrated measurements in act 74.

The deformation sensors 30 measure the bending or twisting in their immediate vicinity. For example, the strain for a plurality of locations along the catheter 18 is determined. In order to improve accuracy for strain gauge measurements, one or more of various instrumentation methods known in the strain gauge art may be used, such as signal averaging, using a Wheatstone bridge to improve common mode rejection, using shielded wires, using twisted pair wires, using a correctly matched instrumentation amplifier, and/or using low resistance wires to link the gauges to the amplifier.

In one embodiment, a look-up table or other memory device is used to convert the local measurements of strain or deformation to bending or twisting moments. The relationship between the measurements and the twisting or bending moments are knows as a function of the type of deformation sensor, such as a strain sensor, and relate to the distance of the deformation sensor 30 from the neutral axis of the catheter 18, such as the center axis of the catheter 18. The neutral axis may be offset from. the center of the catheter 18 as a function of the materials used in the catheter 18. The look-up table is preferably derived from experiment but may be determined from theoretical mathematical calculations. In alternative embodiments, the ultrasound system 10 calculates the twisting and bending moments as they are received.

FIG. 6 shows a graphical representation for determining the position of one local region of the catheter 18. The deformation sensor 30 closest to the handle 24 is spaced 10 centimeters from the handle. In this example, the deformation sensor 30 measures a radius of 50 centimeters in one plane (x, y) and no bending in a second perpendicular plane (z, x). An angle θ is determined from these two values where θ is approximately equal to $$10/2\pi 50 \times 360° = 11.5°.$$

The position of the deformation sensor 30 is determined as a function of these known values and the calculated angle. The position in the x direction or the direction for the measured curve is determined as X=50sin(θ)=9.97 centimeters. Y is determined as y=50−50(cos(θ))=1.0. The deformation sensor 30 closest to the handle is determined as being at x equals 9.97 centimeters, y equals 1.0 centimeters and z equals 0 centimeters in this example. Using the same techniques, the positions of a plurality of deformation sensors 30 are determined and integrated to determine a total position of the catheter 18.

Using the measurements from a plurality of local regions along the catheter 18, the total deformation of the catheter 18 is determined in act 72. For example, linear interpolation of bending moments for regions between the measured regions is determined. Alternatively, curve fitting or other techniques for using the bending or twisting moments from the sampled regions to determine the total deformation of the catheter 18 may be used.

In act 74, the position of the transducer array 20 with respect to the insertion point or handle 24 of the catheter 18 is determined from the integrated measurements. In one embodiment, a plurality of bending measurements is integrated to determine the three-dimensional positioning of the entire length of the catheter 18. With a known position of the transducer array 20 on the catheter 18, the position of the transducer array 20 is determined.

A twisting measurement or integrated twisting measurements is used to determine the rotational displacement of the ultrasound transducer array 20 with respect to a neutral position. Given the known relationship of the neutral position of the catheter 18 with respect to the handle 24, the position and orientation of the ultrasound transducer array 20 with respect to the insertion point or handle 24 is determined. The local measurements are continuously or periodically monitored and the orientation and position information is updated accordingly.

In one embodiment, instrumentation amplifiers within the ultrasound system 10 amplify the measurements from the deformation sensors 30. The amplified information is converted to a digital form for integration and further processing by a processor within the ultrasound system 10. In alternative embodiments, the processor is separate from the ultrasound system 10. In yet other embodiments, an arbitrary origin other than the handle 24 or point of insertion is selected and used as a reference for determining the position and orientation of the ultrasound transducer array 20.

The position of the ultrasound transducer 20 with respect to a known arbitrarily selected origin is used to assist the physician in medical diagnosis. For example, the image on the display 12 is tagged or labeled with position and orientation information. The position and orientation information is provided as numerical figures with the image. As another example, a three-dimensional representation of the catheter position and orientation may also be displayed with the image. In yet other embodiments, the position of the image with respect to a previously scanned three-dimensional representation or a generic representation of the patient is shown with the image. In this embodiment, reference points indicating the size and general outline of the patient as well as the insertion point may be used to more accurately represent the location of the transducer array 20 relative to the patient.

The position and orientation of the transducer array 20 may also be used to assist three-dimensional rendering. For example, a plurality of two-dimensional scans of a patient is obtained using the ultrasound transducer array 20. The ultrasound transducer array 20 is preferably repositioned or reoriented for each of the two-dimensional scans. The position and orientation information for each of the scans is obtained and used to align the image data. A three-dimensional representation is rendered from the aligned image data on the display 12. For an example of three-dimensional rendering, see U.S. Pat. No. 5,928,151, the disclosure of which is incorporated herein by reference. See also U.S. application Ser. No. 09/517,014 filed herewith, the disclosure of which is incorporated herein by reference.

In one embodiment, the deformation sensors 30 are fixedly attached to the catheter 18. In an alternative embodiment, the deformation sensors are removably inserted into a channel of the catheter 18. Many catheters are manufactured with working ports or hollow channels for insertion of additional devices. The catheter 18 is inserted within the patient. A flexible rod sized and shaped for insertion into the hollow central chamber of the catheter 18 is then inserted. The flexible rod with the deformation sensors 30 may be made reusable by isolating the channel from the patient's blood. Measurements of the bending and/or twisting are performed intermittently as the deformation sensors 30 are inserted further into the catheter 18.

To measure the amount of insertion, pinch rollers or other distance measuring devices are used. A single or limited number of bending deformation sensors and a single twisting deformation sensor may then be used to determine the total displacement and orientation of the catheter 18 with respect to the handle 24 or other arbitrary origin. For example, for every 6–10 centimeters of insertion, a local estimate of bending is determined from a bending deformation sensor on the distal portion of the insertion device. These measurements are repeated at intervals, such as 6 or 10 centimeter intervals, until the insertion device has reached the distal end of the catheter 18. Local measurements of bending along the entire length of the catheter 18 are determined. The twisting deformation sensor 30 is positioned on the catheter 18, but may be included on the insertion device. In alternative embodiments, pinch rollers with instrumentation for measuring the advance of the catheter 18 are used as the catheter 18 is inserted. The bending and twisting at one location, such as the distal end of the catheter 18 are periodically measured to estimate the total displacement and orientation of the catheter 18 upon full insertion. This setup allows use of a single bending and a single twisting deformation sensor.

In one embodiment, the rotation of the catheter 18 at or near a point of insertion is measured. The position and orientation of the transducer array 20 is determined as a function of the determined spatial location of the transducer array 20, measured roll of the catheter 18 and any measured twisting.

As an alternative or in additional to strain gauge deformation sensors, fiber-optic sensors may be used. For example, U.S. Pat. No. 5,633,494, the disclosure of which is incorporated herein by reference, discloses scoring fiber optic strands at known locations along the length of the strand. Light loss at the scored areas of the cable due to bending of the cable is measured. Greater amounts of bending result in more light loss. Using multiple fiber optic strands and/or multiple-scored locations, multiple local estimates of bending are measured and integrated to determine the net position and orientation of the catheter 18. Counter wound helical fiber optic strands are used to estimate twisting. One of the two helical wound strands extends while the other contracts. Light loss is measured for both strands. In one embodiment, SHAPE TAPE™ cabling from Measured, Inc. of Fredericton, NB Canada is used, but other fiber optic devices may be used.

Other deformation sensors for determining local amounts of bending and/or twisting may be provided. Furthermore, different types of local deformation sensors may be used in a same catheter 18. Different types of deformation sensors may be used to measure the same or different locations along the length of the catheter 18. For example, a fiber optic deformation sensor and a strain gauge deformation sensor are used to measure the same locations along the catheter 18.

Other position and/or orientation sensors may be used in addition to or as a backup to the plurality of local bending and twisting sensors. For example, magnetic positioning sensors may be used to determine the absolute position and orientation of the transducer array 20.

While the invention has been described above by reference to various embodiments, it will be understood that many changes and modifications can be made without departing from the scope of the invention. For example, different densities or varying densities of deformation sensors may be used. Additional deformation sensing techniques may be developed.

It is therefore intended that the foregoing detailed description be understood as an illustration of the presently preferred embodiments of the invention, and not as a definition of the invention. It is only the following claims, including all equivalents that are intended to define the scope of the invention.

What is claimed is:

1. A medical diagnostic ultrasound imaging catheter for determining a catheter position within a cardiovascular system, the catheter comprising:
   a flexible ultrasound catheter rod comprising a shaft portion and a distal end portion adapted for insertion into a patient;
   an ultrasound transducer operatively connected with the distal end portion; and
   a plurality of local deformation sensors spaced along the ultrasound catheter rod.

2. The catheter of claim 1 wherein the local deformation sensors comprise strain gauges.

3. The catheter of claim 1 wherein the local deformation sensors comprise at least one fiber optic strand.

4. The catheter of claim 1 wherein the plurality of local deformation sensors are fixedly attached to the catheter rod.

5. The catheter of claim 1 wherein the catheter rod further comprises an internal channel and the plurality of local deformation sensors are removably positionable within the internal channel.

6. The catheter of claim 1 wherein the plurality of local deformation sensors comprise sensors sensitive to local catheter bending.

7. The catheter of claim 1 wherein the plurality of local deformation sensors comprise sensors sensitive to local catheter twisting.

8. The catheter of claim 1 wherein each of the plurality of local deformation sensors comprises a pair of strain gauges, at least one pair of strain gauges along a first plane through an axis of the catheter rod and at least one pair of strain gauges along a second plane through the axis, the second plane at about a 90 degree angle to the first plane.

9. The catheter of claim 6 wherein the bend sensors are spaced along the catheter rod at least three locations and further comprising at least one twist strain gage positioned at the distal end portion.

10. A method for determining a position of a medical diagnostic ultrasound imaging catheter within a cardiovascular system, the method comprising the acts of:
   (a) measuring a local deformation at each of a plurality of locations along the ultrasound imaging catheter while inserted in a patient;
   (b) integrating the local deformation measurements; and
   (c) determining a position of an ultrasound transducer array as a function of (b).

11. The method of claim 10 wherein (a) comprises measuring strain at the plurality of locations.

12. The method of claim 10 wherein (a) comprises measuring light loss at the plurality of locations.

13. The method of claim 10 wherein (a) comprises measuring at fixed locations.

14. The method of claim 10 further comprising:
   (d) removably inserting a shaft comprising at least one deformation sensor.

15. The method of claim 10 wherein (a) comprises measuring an amount of bend.

16. The method of claim 10 wherein (a) comprises measuring an amount of twist.

17. The method of claim 10 further comprising:
   (d) positioning multiple sets of strain gauges at each of the plurality of locations.

18. The method of claim 10 wherein (a) comprises:
   (a1) measuring an amount of bend at each of the plurality of locations along the catheter; and
   (a2) measuring an amount of twist at the distal end of the catheter.

19. The method of claim 10 wherein (b) comprises fitting the local deformation measurements to a curve.

20. The method of claim 10 further comprising:
   (d) interpolating moment data associated with positions between the plurality of locations.

21. The method of claim 10 further comprising:
   (d) aligning image data as a function of the position of the ultrasound transducer.

22. The method of claim 10 further comprising:
   (d) producing a 3D image data set as a function of the position of the ultrasound transducer.

23. A medical diagnostic ultrasound imaging catheter for determining a catheter position within a cardiovascular system during use of the catheter, the catheter comprising:
   a flexible ultrasound catheter rod comprising a shaft portion and a distal tip portion;
   an ultrasound transducer operatively connected with the distal tip portion;

at least one strain gauge around a circumference of the ultrasound catheter rod; and a plurality of strain gauges spaced apart along the catheter rod.

24. The catheter of claim 23 wherein the strain gauges are placed closer together on a more flexible portion than on a less flexible portion of the catheter.

25. The method of claim 10 further comprising:

(d) measuring a rotation at an insertion point;

wherein the determined position is responsive to the measured rotation.

* * * * *